United States Patent [19]
Sheftel et al.

[11] Patent Number: 5,658,750
[45] Date of Patent: Aug. 19, 1997

[54] METHOD FOR LIMITING THE COURSE OF TREATMENT FOR AN INFESTATION OF LICE

[75] Inventors: Miriam Sheftel, 487 Ward St., Newton Centre, Mass. 02159; David Kagan, Lakewood, N.J.

[73] Assignee: Miriam Sheftel, Mewton Centre, Mass.

[21] Appl. No.: 560,937

[22] Filed: Nov. 20, 1995

Related U.S. Application Data

[63] Continuation-in-part of Ser. No. 357,322, Dec. 16, 1994, abandoned.

[51] Int. Cl.$^6$ ............................ C12Q 1/02; C12Q 1/22
[52] U.S. Cl. .................................. 435/29; 435/31
[58] Field of Search ...................... 435/29, 31, 32, 435/34, 968; 436/800, 805, 811, 905

[56] References Cited

U.S. PATENT DOCUMENTS

| | | | |
|---|---|---|---|
| 4,532,707 | 8/1985 | Allen | 30/200 |
| 5,072,746 | 12/1991 | Kantor | 132/219 |
| 5,227,163 | 7/1993 | Eini et al. | 424/195.1 |
| 5,261,427 | 11/1993 | Dolev | 132/200 |
| 5,273,746 | 12/1993 | Payne et al. | 424/932 |
| 5,286,749 | 2/1994 | Kieran et al. | 514/531 |

OTHER PUBLICATIONS

Owen R. R., Improved in vitro Determination of the Viability of Taenia Embryos, Annals of Tropical Medicine and Parasitology, 79 (6) 655–656. Dec. 1985.

Sokoloff F., Identification and Management of Pediculosis, The Nurse Practitioner 19(8) 62–64. Aug. 1994.

*Primary Examiner*—Ralph Gitomer
*Attorney, Agent, or Firm*—Cesari and McKenna

[57] ABSTRACT

Methods of detecting louse infestations and monitoring the course of insecticidal treatments are disclosed. Samples of hair or suspected egg cases removed from the hair are exposed to a vital indicator to provide a visual, colorimetric indication of their viability. In one embodiment, the indicator changes color by an amount directly related to cell metabolic activity; following exposure, the egg casing(s), or a solution containing them and the agent, are compared with a color chart having multiple, differently colored entries, each entry corresponding to a different degree of cell viability. From this comparison, an indication of viability, corresponding to the progress of treatment or the presence of an infestation, is obtained. In other embodiments, the viability indicator is a colored material taken up by live cells but not dead ones, or by dead cells but not live ones; the free material is washed away following exposure, after which the egg casing(s) themselves are visually inspected. Once again, the degree of color change indicates cell viability.

10 Claims, No Drawings

METHOD FOR LIMITING THE COURSE OF TREATMENT FOR AN INFESTATION OF LICE

RELATED APPLICATION

This is a continuation-in-part of U.S. Ser. No. 08/357,322, filed Dec. 16, 1994, and now abandoned.

BACKGROUND OF THE INVENTION

1. Field of the Invention

The present invention relates to treatment of louse infestations, and in particular to monitoring and affecting the course of such treatment.

2. Description of the Related Art

Lice represent an increasingly prevalent social and health problem in many countries, including the United States. Lice spread rapidly by contact; infestations can therefore occur even under relatively sanitary conditions and, given the ease of modern travel and immigration, appear even in normally pest-free environments.

Lice infest both humans and animals. They produce irritations typically experienced as uncomfortable local itching and burning, occupying regions under matted fur (in animals) and the ears, head, neck and shoulders (in humans). More serious infestations can cause infection, anemia and fever. Three major diseases—epidemic typhus, trench fever and relapsing fever—are transmitted by lice. The species most troublesome to humans are the head lice *Pediculus capitis* or *Pediculus humanus capitis;* the body or clothing lice *Pediculus humanus humanus* or *Pediculus corporis;* and the pubic lice *Phthirius pubis*.

The parasites themselves are insects that are very small (two to three millimeters in length) and not easily observed without magnification. They attach themselves to hair and fur shafts near the bases, where they lay eggs, frequently called "nits," that become firmly attached to hair and fur through an adhesive excretion. The eggs resemble white gains of sand and are easily mistaken for dandruff; at body temperature, they generally hatch in eight to 10 days. Because of the small size of the louse and its nits, detection by visual inspection can be difficult. The difficulty increases as treatment progresses and the concentration of visually apparent particles decreases.

Numerous methods of treatment have been devised to combat louse infestations; unfortunately, even when fully effective, these tend to result in side effects, and are at the very least inconvenient and expensive. Accordingly, determining when the lice have been fully eliminated can avoid needless prolongation of harsh treatments. Likewise, detecting infestations or re-infestations (which can occur, for example, from wearing an infested garment) at the earliest possible stage will minimize the duration of treatment.

The most common form of treatment is the frequent use of an insecticidal shampoo that is toxic both to the louse and the egg. The harsh nature of the active ingredients in such preparations, however, can prevent or restrict their use by certain susceptible individuals and very young children; moreover, the lice themselves can build up resistance to insecticidal products even during the course of treatment, necessitating prolonged application that can cause discomfort even in adults. Head lice are also treated using heated or electrically charged hair combs; see, e.g., U.S. Pat. No. 5,261,427. The efficacy of these approaches typically depends on physical contact between the comb and the lice and/or eggs, requiring extensive applications that can irritate the human scalp.

Thus, using current techniques, the treatment agent is applied to the infestation for a fixed period that is sufficiently long to ensure the probable eradication of the infestation—regardless of the actual severity of that infestation, the susceptibility of the particular lice to treatment, or the adverse effects of treatment on the individual. While the mere existence of an infestation can be detected by visual inspection, such inspection cannot indicate the infestation's extent or the optimal amount of treatment to eradicate it. There is, accordingly, a long-felt and heretofore unmet need for limiting the course of treatment for louse infestations to the extent possible while assuring overall treatment efficacy.

DESCRIPTION OF THE INVENTION

Objects of the Invention

It is, therefore, an object of the present invention to provide a reliable indicator of the progress of treatments for louse infestations.

It is another object of the invention to avoid unnecessary prolongation of lice-eradicating treatments.

It is yet another object of the invention to allow the efficacy and progress of louse treatments to be measured by convenient, quantitative means.

It is a further object of the invention to avoid inconclusive visual inspections of the hair and scalp to identify louse infestations and their persistence.

Other objects will, in part, be obvious and will, in part, appear hereinafter. The invention accordingly comprises the several steps and the relation of one or more of such steps with respect to the others as exemplified in the following description, and the scope of the invention will be indicated in the claims.

DETAILED DESCRIPTION OF THE INVENTION

The foregoing objects are accomplished by subjecting samples of hair or fur, or suspected egg cases removed from the hair or fur, to a vital indicator to determine their viability. If an egg exhibits signs of metabolism, it is potentially viable, and the persistence of infestation is suggested; if a sufficient number of eggs is non-viable, the infestation has probably been eradicated. The present invention can therefore also be used to quickly and conveniently discriminate between louse infestations and acute cases of dandruff, where simple visual inspection would yield inconclusive results. Most preferably, however, the invention permits louse treatment to be tailored to the characteristics of a particular infestation, avoiding the current "one size fits all" approach that can overtreat the subject.

In one embodiment, the vital indicator responds to enzymes characteristic of living organisms. For example, 3-(4,5-dimethylthiazol-2-yl)-2,5-diphenyltetrazolium bromide ("MTT", sometimes called thiazolyl blue) is known to respond to mitochondrial enzymes, which transform dissolved MTT into an insoluble, dark blue formazon salt. Only a live parasite egg, therefore, will turn the MTT solution blue.

In a working implementation of this approach, one or more suspected egg cases are removed from the skin, hair or fur using a pair of forceps or an adhesive pad. The eggs are transferred to a vial containing 250 µl of an aqueous MTT solution, specifically, 0.5 mg/ml MTT in phosphate-buffered saline at pH 7. This solution is yellow. The vial is then shaken to ensure that the egg casings are fully covered, and the solution incubated at room temperature as necessary (generally 2–3 hours or less). The degree of color change to blue reflects the amount of metabolic activity associated with the eggs. Accordingly, while the presence of a blue color itself suffices to indicate egg viability and the continued presence infestation, visual comparison of the observed color to a calibrated color chart can supply information regarding the progress of insecticidal treatment: since these agents often do not kill immediately, the amount of remaining metabolic activity indicates the ratio of live to dead eggs, and therefore the extent to which treatment must be continued. Since metabolic activity is indicated by the intensity of the blue MTT color, only when the color associated with multiple egg casings remains mostly yellow (or exhibits a sufficiently small transition to blue to confirm widespread eradication) is it advisable to discontinue treatment.

Thus, practice of the invention involves periodically obtaining a plurality of suspected louse egg casings from the subject during the course of treatment; exposing the egg casings (together or serially) to the vital indicator; observing the exposed casings for a visual indication of metabolic activity; determining, from the visual indication, an approximate ratio of louse egg casings that exhibit metabolic activity to louse egg casings that do not; and terminating application of the treatment agent when the ratio indicates substantial eradication of the infestation. The result is a shortened course of treatment.

Other assays for enzymatic activity associated only with live cells, such as the well-known hexoseaminidase assay (analogous to the MTT test but reflecting the activity of a different vital enzyme), can furnish suitable alternatives to the MTT test described above. More generally, other tests that provide a visual indication of viability can be used as well. For example, carboxy-methyl ester is converted to a fluorescent product by live cells but not dead cells. Application of this compound to a suspected nit, in proportions and in accordance with incubation techniques well-known in the art, can likewise provide the detection function in this embodiment of the invention.

In a second embodiment, eggs are exposed to chemical agents that are taken up by live cells but not dead ones. These include neutral red dye (C.I. 50040, 3-amino-7-dimethylamino-2-methylphenazine hydrochloride) and erythrosin B (C.I. 45430:2, solvent red 140). In this embodiment, at least one egg (and preferably a cluster, given their small size) is exposed to the agent and then washed. Transformation of the initial whitish appearance to the color of the chemical agent indicates uptake and, therefore, viability. Accordingly, as in the first embodiment, the degree of color change reflects the amount of uptake and visually indicates the overall extent of viability. Once again, comparison with a color chart indicates the efficacy of treatment and whether it must be continued.

In a third embodiment, eggs are exposed to chemical agents that are taken up by dead cells but not live ones; such agents include Nigrosin or Trypan Blue (G.I. 23850). In this embodiment, an egg or, preferably, a cluster of eggs is exposed to the agent and subsequently washed. In this case, the stronger the observed color, the more effective the treatment has been.

It will therefore be seen that we have developed a highly versatile technique for discriminating between viable and non-viable nits, and using the results to direct the course of treatment. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of limiting the course of treatment for an infestation of lice, the method comprising the steps of:

a. treating the infestation by applying a treatment agent to a subject;

b. providing a chemical agent that provides a visual indication of cell metabolic activity;

c. periodically obtaining a plurality of louse egg casings from the subject during the course of treatment;

d. exposing the egg casings to the chemical agent;

e. observing the exposed casings for the visual indication;

f. determining a ratio of louse egg casings that exhibit metabolic activity to louse egg casings that do not; and g. terminating application of the treatment agent when the ratio indicates substantial eradication of the infestation, thereby shortening the course of treatment.

2. The method of claim 1 wherein the visual indication is provided by a colorimetric assay wherein an observable color indicates a degree of egg casing metabolic activity.

3. The method of claim 2 further comprising the steps of:

a. providing a color chart having multiple, differently colored entries, each entry corresponding to a different degree of egg casing metabolic activity;

b. comparing the exposed egg casings to the color chart to find the entry whose color most closely matches that of the exposed egg casings; and c. determining the ratio of louse egg casings that exhibit metabolic activity to louse egg casings that do not based on successive comparisons.

4. The method of claim 2 wherein the chemical agent changes color to reflect the degree of egg casing metabolic activity.

5. The method of claim 4 wherein the chemical agent is contained in solution, and the solution containing the chemical agent and the egg casing are observed for the visual indication.

6. The method of claim 4 wherein the chemical agent is 3-(4,5-dimethylthiazol-2-yl)-2,5-diphenyltetrazolium bromide.

7. The method of claim 4 wherein the chemical agent is carboxy-methyl ester.

8. The method of claim 1 wherein the chemical agent is absorbed by louse egg casings that exhibit metabolic activity but not by louse egg casings that do not, the method further comprising the step of, following the observing step, washing the egg casings to remove unabsorbed chemical agent.

9. The method of claim 8 wherein the chemical agent is neutral red dye.

10. The method of claim 8 wherein the chemical agent is erythrosin B.

* * * * *